United States Patent [19]

Then et al.

[11] Patent Number: 5,587,319
[45] Date of Patent: Dec. 24, 1996

[54] PROCESS FOR THE PREPARATION OF L-PHOSPHINOTHRICIN USING TRANSAMINASES OF DIFFERENT SPECIFICITIES IN A LINKED PROCESS

[75] Inventors: Johann Then, Frankfurt am Main; Werner Aretz, Königstein; Klaus Sauber, Bad Soden am Taunus, all of Germany

[73] Assignee: Hoechst Aktiengesellschaft, Frankfurt am Main, Germany

[21] Appl. No.: 272,286

[22] Filed: Jul. 8, 1994

Related U.S. Application Data

[63] Continuation of Ser. No. 136,605, Oct. 15, 1993, abandoned, which is a continuation of Ser. No. 879,111, May 4, 1992, abandoned, which is a continuation of Ser. No. 448,814, Dec. 12, 1989, abandoned.

[30] Foreign Application Priority Data

Dec. 14, 1988 [DE] Germany .......................... 38 42 025.2

[51] Int. Cl.$^6$ ............................. C12P 41/00; C12P 19/02
[52] U.S. Cl. ................................... 435/280; 435/106
[58] Field of Search ..................... 435/280, 106

[56] References Cited

U.S. PATENT DOCUMENTS

| | | | |
|---|---|---|---|
| 4,168,963 | 9/1979 | Rupp et al. ......................... | 71/86 |
| 4,226,941 | 10/1980 | Goi et al. ........................... | 435/280 |
| 4,304,858 | 12/1981 | Wandley et al. ................... | 435/106 X |
| 4,518,692 | 5/1985 | Rozzell ............................... | 435/106 |
| 4,603,111 | 7/1986 | Keller et al. ....................... | 435/182 |
| 4,745,059 | 5/1988 | Voelskow et al. ................. | 435/108 |
| 4,745,061 | 5/1988 | Aretz et al. ........................ | 435/280 |
| 4,826,766 | 5/1989 | Rozzell ............................... | 435/106 |
| 4,950,606 | 8/1990 | Stirling et al. ..................... | 435/280 |
| 5,130,246 | 7/1992 | Schultz et al. ..................... | 435/193 |
| 5,162,212 | 11/1992 | Schultz et al. ..................... | 435/128 |

FOREIGN PATENT DOCUMENTS

| | | | |
|---|---|---|---|
| 73794/87 | 12/1987 | Australia . | |
| 1241146 | 8/1988 | Canada . | |
| 135846 | 4/1985 | European Pat. Off. ......... | 435/106 |
| 248357 | 5/1987 | European Pat. Off. . | |
| 249188 | 12/1987 | European Pat. Off. ......... | 435/106 |
| 0315786A1 | 5/1989 | European Pat. Off. . | |
| 374651 | 6/1990 | European Pat. Off. ......... | 435/106 |
| 2438054 | 4/1980 | France . | |
| 8701727 | 3/1987 | WIPO ................................ | 435/106 |

OTHER PUBLICATIONS

Dixon and Webb, Enzymes pp. 75–80 (1964).
Chemical Abstract, vol. 69, No. 58390t (1968).

*Primary Examiner*—Irene Marx
*Assistant Examiner*—S. Saucier
*Attorney, Agent, or Firm*—Finnegan, Henderson, Farabow, Garrett & Dunner, L.L.P.

[57] ABSTRACT

L-2-Amino-4-methylphosphinobutyric acid can be prepared by a racemate resolution in the presence of D-aminoacid and L-aminoacid transaminases by reaction with α-keto acids and amino-group donors. In particular, transaminases from *Bacillus licheniformis* and from *Escherichia coli* are used.

11 Claims, No Drawings

PROCESS FOR THE PREPARATION OF L-PHOSPHINOTHRICIN USING TRANSAMINASES OF DIFFERENT SPECIFICITIES IN A LINKED PROCESS

This application is a continuation of application Ser. No. 08/136,605, filed Oct. 15, 1993, now abandoned, which was a continuation of application of Ser. No. 07/879,111, filed May 4, 1992, now abandoned, which was a continuation of application of serial No. 07/448,814, filed Dec. 12, 1989, now abandoned.

L-2-Amino-4-methylphosphinobutyric acid (called L-phosphinothricin or L-PTC hereinafter) or the salts thereof are—as has already been disclosed in German Offenlegungsschrift 29 39 269—the active component of the racemates which are easy to obtain chemically. According to German Offenlegungsschrift 27 17 440, the latter have a very good and broad herbicidal activity against many monocotyledons and dicotyledons, annual and perennial weeds. Since L-PTC and its abovementioned derivatives have about twice the activity of the racemates, it is desirable to develop a process with which it is possible to make L-PTC obtainable in a simple manner in relatively large amounts.

The resolution of the D,L-phosphinothricin racemate as well as the conversion of D-PTC into L-PTC, can be carried out in a straightforward manner using a D-aminoacid transaminase and an L-aminoacid transaminase.

Hence the invention relates to a process for the preparation of L-2-amino-4-methylphosphinobutyric acid, which comprises reacting D,L-2-amino-4-methylphosphinobutyric acid with α-keto acids and amino-group donors in the presence of D-aminoacid and L-aminoacid transaminases.

The invention is explained in detail hereinafter, in particular in its preferred embodiments. The invention is also defined in the claims.

The D-aminoacid transaminase can be obtained from *Pseudomonas putida* and *Bacillus licheniformis* (German Offenlegungsschrift 34 47 023 and Netherlands Published Specification 87 02 449). The D-transaminase which is described in German Offenlegungsschrift DE 34 47 023 and is isolated from *Bacillus licheniformis* ATCC 9945 is preferably employed.

It is possible to use as L-aminoacid transaminase the corresponding enzymes from *E. coli, Paracoccus denitrificans*, Torula or Rhodotorula (German Offenlegungsschrift 34 23 936). Preferably used in this case is the L-transaminase from *E. coli* ATCC 11303, which has also been described, for example, in J. Then et al., Biotechnology Letters 9 (10), 680–684 (1987).

The racemate resolution according to the invention is divided into two reaction steps 1. D-Amino acid transamination:
   D,L-phosphinothricin+
   α-keto acid, in the presence of
   D-aminoacid transaminase yields
   D-amino acid+3-carboxy-3-oxo-propylmethylphosphinate+
   L-phosphinothricin
and subsequently
2. L-amino acid transamination:
   3-carboxy-3-oxo-propylmethylphosphinate+
   L-amino acid, in the presence of
   L-aminoacid transaminase yields
   L-phosphinothricin+
   α-keto acid.

For carrying out the reaction according to the invention it is possible in each case to employ the enzymes which have been isolated by processes known per se or else the whole cells in free or immobilized form.

The amino-group donor employed for the first reaction step is preferably D,L-PTC, and for the second reaction step is L-asparagine, glycine, L-aspartic acid and L-glutamic acid. The amino acids are used in the form of their free acids or suitable salts.

Preferably used as α-keto acid in the first reaction step are phenylglyoxylate, 4-hydroxyphenylglyoxylate and thiophenylglyoxylate.

The amount of D-aminoacid transaminase in the reaction mixture can vary within a wide range. It is expediently in a range from 0.05 to 50 μmol/min.ml. The mixture preferably contains 0.1 to 2 μmol/min.ml.

The PTC racemic mixture is expediently employed in twice the molar amount relative to the α-keto acid. In order, where possible, to displace the equilibrium towards the final product of the reaction, the α-keto acid is employed in slightly larger amounts.

The reaction components can be added to the reaction mixture as solution in water or as solid substances simultaneously. However, stepwise addition in amounts of 1 to 5%, in particular 1.5 to 4.5%, in each case relative to the reaction mixture, over a period of 1 to 90 hours is preferred. A pH between 5 and 9, in particular between 7 and 8.5, is advantageously used. It is furthermore expedient to carry out the reaction in a temperature range from 20° to 65° C.

The amount of L-aminoacid transaminase enzyme in the reaction mixtures can be selected from a wide range. It is expediently between 10 and 20,000 μmol/min.l. The mixture preferably contains enzyme in amounts of 1,500 to 20,000 μmol/min.l.

The amino-group donor for the L-aminoacid transaminase is employed in equimolar amounts or in excess relative to the α-keto acid which is formed in the first reaction step. Ratios of 1:1 to 5:1, advantageously 1:1 to 2:1, have proven appropriate. The amino-group donor is added either immediately or stepwise throughout the reaction time. An advantageous pH is between 5 and 9, in particular between 7 and 8.5. It is also advantageous to carry out the reaction in a temperature range from 20° to 65° C.

The process is particularly preferably carried out as a so-called "one-pot process". This entails enzymes L-aminoacid transaminase and D-aminoacid transaminase being used together in solution or bound to a carrier as described in DOS 32 37 341 or in DOS 33 44 912. The reaction components are likewise added together to a mixture. This "one-pot process" can be used so advantageously in particular because the L-aminoacid transaminase does not react with the α-keto acids in the first reaction step, phenylglyoxylate, 4-hydroxyphenylglyoxylate and thiophenylglyoxylate as substrate. The D-aminoacid transaminase, on the other hand, does not react with the L-amino acids in the second reaction step. Furthermore, the enzymes react in the same pH and temperature range.

The racemate resolution according to the invention has the following advantages by comparison with conventional processes for the resolution of D,L-phosphinothricin racemates:

no salt loading as a consequence of setting up very different pH values, such as, for example, in the racemate resolution using penicillin -G acylase.

No losses as in thermal racemization. It is possible to prepare not only L-PTC as valuable product but also, in addition, another D-amino acid too.

EXAMPLE 1

The following reaction mixture was incubated with D-aminoacid transaminase from *Bacillus licheniformis* ATCC 9945 (DOS 34 47 023, Examples 1 to 4, see annex):

| | | |
|---|---|---|
| D,L-phosphinothricin | (200 mM) | 0.2 ml |
| α-keto acid | (100 mM) | 0.2 ml |
| Potassium phosphate buffer | (50 mM; pH 8.0) | 0.3 ml |
| Pyridoxal phosphate | (200 μg/ml) | 0.05 ml |
| D-aminoacid transaminase crude extract (Example 3, annex) | | 0.25 ml |

The mixtures were shaken at 180 rpm and 37° C. for 24 hours. The results are shown in the following table:

| Amino-group donor | Amino-group acceptor | Reaction |
|---|---|---|
| D,L-Phosphinothricin | Pyruvate | + |
| D,L-Phosphinothricin | Phenylpyruvate | ++ |
| D,L-Phosphinothricin | 4-Hydroxyphenylglyoxylate | ++ |

1 μl samples from the above mixtures were applied to silica gel thin-layer plates and fractionated in the mobile phase butanol/glacial acetic acid/water (4:1:1). The identification was carried out by means of reference substances after spraying with ninhydrin.

| | |
|---|---|
| ++ | good reaction |
| + | distinct reaction |

To measure the D-aminoacid transaminase activity, D-α-aminoadipic acid (20 mmolar), α-ketoglutarate (10 mmolar) and pyridoxal phosphate (10 μg/ml) are incubated with the enzyme in potassium phosphate buffer (10 mmolar), pH 8, at a temperature of 37° C. This results in the formation of D-glutamic acid which can be determined by thin-layer chromatography after spraying with ninhydrin.

EXAMPLE 2

Preparation of L-aminoacid transaminase E. coli ATCC 11303 was cultured in the following nutrient solution.

| | |
|---|---|
| Fumaric acid | 5 g/l |
| Meat extract | 20 g/l |
| Aspartic acid | 20 g/l |
| KH$_2$PO$_4$ | 2 g/l |
| MgSO$_4$ · 7H$_2$O | 0.5 g/l |
| CaCl$_2$ · 2H$_2$O | 0.1 g/l; pH 7.2 |

After shaking at 200 rpm and 37° C. for 20 hours, the cells were suspended in potassium phosphate buffer (50 mM, pH 7.4) and spun down. The cells were subsequently taken up again in 1 ml of phosphate buffer per g of cells and disrupted by addition of 27 μmol/l N-cetyl-N,N,N-trimethylammonium bromide. The suspension was subsequently centrifuged again. The L-aminoacid transaminase is to be found in the supernatant.

EXAMPLE 3

A reaction mixture of D,L-phosphinothricin and 4-hydroxyphenylglyoxylate of total volume 5 ml was incubated with D-aminoacid transaminase for 24 h as in Example 1. Then 0.02 g of sodium L-aspartate plus 0.3 ml of L-aminoacid transaminase crude extract from Example 2—total enzyme activity 30 μmol/min—were added. The reaction mixture was adjusted to pH 7.4 HCl and incubated at 37° C., shaking for a further 24 hours.

The α-aminoacid transaminase activity was determined using the Sigma G 0390 assay kit. 12 mmol/l of sodium phenylpyruvate was employed in place of α-ketoglutarate.

It was possible, with the aid of analytical HPLC on RP18 columns, to measure 33 mmol/l L-phosphinothricin after the reaction was complete.

EXAMPLE 4

Specificity of the L-aminoacid transaminase

The specificity of the L-aminoacid transaminase from E. coli ATCC 11303 was determined using the enzyme assay for the transaminase measurement according to the Sigma G 0390 assay kit. Aspartic acid was used as amino-group donor.

The α-keto acid 2-oxoglutarate was replaced by other α-keto acids (see table). The initial reaction rates in the enzyme assay were compared with one another, with that for phenylpyruvate being defined as 100%. The table which follows shows the activities measured:

| α-Keto acid | Transaminase activity (%) |
|---|---|
| Phenylpyruvate | 100 |
| 3-carboxy-3-oxo-propyl-methylphosphinate | 110 |
| 2-Oxoglutarate | 96 |
| Dimethylpyruvate | 82 |
| Phenylglyoxylate | 5 |
| 4-Hydroxyphenylglyoxylate | 5 |
| Thiophenylglyoxylate | 2 |

Annex to the examples

Isolation of D-aminoacid transaminase from Bacillus licheniformis ATCC 9945 according to DOS 34 47 023, Examples 1 to 4:

EXAMPLE 1

The strain Bacillus licheniformis ATCC 9945 is maintained on slant tubes of the following composition:

0.3% Bacto beef extract 0.5% Bacto peptone 1.5% agar (pH 7.0)

After incubation at 30° C. for a period of 2–3 days the spores are rinsed out with 10 ml of physiological saline, and 1 ml of this suspension is used to inoculate 100 ml of preculture of the following composition:

1% yeast extract 0.8% nutrient broth 0.5% maltose (pH 7.5)

The flask is incubated at 3° C. and 190 rpm on a rotary shaker for 24 hours. 50 ml of this preculture are subsequently introduced into Erlenmeyer flasks of capacity 2 l, each containing 500 ml of nutrient solution and shaken as main culture at 30° C. and 190 rpm for 24 hours:

Main culture medium:

1% yeast extract 0.8% nutrient broth 0.5% D,L-glutamic acid (pH 7.2)

The D-aminoacid transaminase (DATA) activity reaches its maximum in the stationary phase of growth.

EXAMPLE 2

*Bacillus licheniformis* ATCC 9945 is cultured in a pre-culture (500 ml) as described in Example 1 and, after 24 hours, used to inoculate a 12 l fermenter containing 9 l of the abovementioned main culture nutrient medium. The fermentation time at 30° C., an aeration rate of 0.15 vvm and 300 rpm is 22–26 hours. The DATA activity corresponds to that in Example 1.

EXAMPLE 3

The cell disruption necessary to isolate the DATA is carried out by enzymatic means. For this purpose, the cells which have been taken up (0.5 g/ml) in potassium phosphate buffer (pH 7.0, 10 mM+10 µm pyridoxal phosphate) are mixed with 1 mg of lysozyme/ml of cell suspension and incubated at 190 rpm and 30° C. for 10–30 minutes. After a microscopic check the incubation mixture is centrifuged, and the supernatant is further processed as crude extract. The enzyme activity in the crude extract is 0.5 µmol/min.ml.

EXAMPLE 4

The crude extract obtained as in Example 3 is subjected to a fractional ammonium sulfate precipitation:

208 ml of the crude extract are mixed with ammonium sulfate to 30% of saturation and centrifuged. The supernatant is mixed with further ammonium sulfate to 60% of saturation and spun down. The precipitate is taken up in 22 ml of phosphate buffer (10 mM, pH 8.0), which contains 10 µM pyridoxal phosphate, and dialyzed against the same buffer for one night.

We claim:

1. A two step process for the preparation of L-2-amino-4-methylphosphinobutyric acid, which comprises:
   (a) reacting D,L-2-amino-4-methylphosphinobutyric acid with an α-keto acid, catalyzed by a D-aminoacid transaminase to produce 3-carboxy-3-oxo-propylmethylphosphinate, wherein said α-keto acid, is phenylglyoxylate, 4-hydroxyphenylglyoxylate or thiophenylglyoxylate, and
   (b) reacting the 3-carboxy-3-oxo-propylmethylphosphinate with an amino-group donor wherein said amino-group donor is L-asparagine, L-aspartic acid, L-glutamic acid or glycine, catalyzed by an L-amino transaminase, wherein said D-aminoacid transaminase does not substantially react with the amino-group donor employed in step (b), and said L-aminoacid transaminase does not substantially react with the α-keto acid employed in step (a) to obtain a product:
   (c) separating L-2-amino-4-methylphosphinobutyric acid from the product obtained in step (b).

2. The process as claimed in claim 1, wherein D-aminoacid transaminase is obtained from *Bacillus licheniformis* ATCC 9945.

3. The process as claimed in claim 1, wherein L-aminoacid transaminase is obtained from *E. coli* ATCC 11303.

4. The process as claimed in claim 1,
   wherein the reaction is carried out at a pH between 5 and 9.

5. The process as claimed in claim 4, wherein the pH is between 7 and 8.5.

6. The process as claimed in claim 1,
   wherein the reaction temperature is between 20° and 65° C.

7. The process of claim 1 where said α-keto acid is reacted with said D,L-2-amino-4-methylphosphinobutyric acid by stepwise addition to said D,L-2-amino-4-methylphosphinobutyric acid and said amino group donor is reacted with said 3-carboxy-3-oxo-propylmethylphosphinate by stepwise addition to said 3-carboxy-3-oxo-propylmethylphosphinate.

8. A two step process for the preparation of L-2-amino-4-methylphosphinobutyric acid which comprises:
   (a) reacting D,L-2-amino-4-methylphosphinobutyric acid with an α-keto acid, catalyzed by a D-amino acid transaminase to produce 3-carboxy-3-oxo propylmethylphosphinate, wherein said α-keto acid is phenylglyoxylate, 4-hydroxyphenylglyoxylate or thiophenylglyoxylate, and
   (b) reacting the 3-carboxy-3-oxo-propylmethyl-phosphinate with an amino-group donor wherein said amino-group donor is L-asparagine, L-aspartic acid, L-glutamic acid or glycine, catalyzed by a L-aminoacid transaminase, wherein said D-aminoacid transaminase does not substantially react with the amino-group donor employed in step (b) and said L-amino transaminase does not substantially react with the α-keto acid employed in step (a), said process being carried out as a one pot process to obtain a product;
   (c) separating L-2-amino-4-methylphosphinobutyric acid from the product obtained in step (b).

9. A two step process for the preparation of L-2-amino-4-methylphosphinobutyric acid, which comprises:
   (a) reacting D,L-2-amino-4-methylphosphinobutyric acid with an α-keto acid, catalyzed by a D-amino acid transaminase to produce 3-carboxy-3-oxo-propylmethyphosphinate, wherein said α-keto acid is phenylglyoxylate, 4-hydroxyphenylglyoxylate or thiophenylglyoxylate; and
   (b) reacting the 3-carboxy-3-oxo-propylmethyl-phosphinate with an amino-group donor wherein said amino-group donor is L-asparagine, L-aspartic acid, L-glutamic acid or glycine, catalyzed by an L-aminoacid transaminase, wherein said D-aminoacid transaminase does not substantially react with the amino-group donors employed in step (b) and said L-aminoacid transaminase does not substantially react with the α-keto acids employed in step (a), wherein the D-aminoacid transaminase is obtained from *Bacillus licheniformis* ATCC 9945 and wherein the L-aminoacid transaminase is obtained from *E. coli* ATCC 11303, to obtain a product;
   (c) separating L-2-amino-4-methylphosphinobutyric acid from the product obtained in step (b).

10. The process of claim 12 carried out as a one-pot process.

11. The process of any one of claims 8, 9, or 10 where said α-keto acid is reacted with said D,L-2-amino-4-methylphosphinobutyric acid by stepwise addition to said D,L-2-amino-4-methylphosphinobutyric acid and said amino group donor is reacted with said 3-carboxy-3-oxo-propylmethylphosphinate by stepwise addition to said 3-carboxy-3-oxo-propylmethylphosphinate.

* * * * *

UNITED STATES PATENT AND TRADEMARK OFFICE
CERTIFICATE OF CORRECTION

PATENT NO. : 5,587,319
DATED : December 24, 1996
INVENTOR(S) : Johann THEN et al.

It is certified that error appears in the above-indentified patent and that said Letters Patent is hereby corrected as shown below:

Claim 1, column 5, line 41, after "acid" delete ",".

Claim 3, column 5, line 58, after "wherein" insert --the--.

Claim 8, column 6, line 23, begin new unindented line with word --wherein--.

Claim 10, column 6, line 54, "claim 12" should read --claim 9--.

Signed and Sealed this

Second Day of February, 1999

Attest:

*Attesting Officer*

*Acting Commissioner of Patents and Trademarks*